United States Patent [19]

Haviv et al.

[11] 4,370,339
[45] Jan. 25, 1983

[54] METHOD FOR TREATING INFLAMMATORY CONDITIONS

[75] Inventors: Fortuna Haviv, Deerfield; Robert W. DeNet, Waukegan; William A. Boulanger, Urbana, all of Ill.

[73] Assignee: Abbott Laboratories, North Chicago, Ill.

[21] Appl. No.: 301,475

[22] Filed: Sep. 14, 1981

[51] Int. Cl.³ .......................................... A61K 31/415
[52] U.S. Cl. ................................................. 424/273 P
[58] Field of Search ................ 424/273, 273 R, 273 P

[56] References Cited

U.S. PATENT DOCUMENTS 3,927,025 12/1975 Korbonitis et al. ................. 424/263

OTHER PUBLICATIONS

Chem. Abst., Chem. Subst. Index Pp–Z, vol. 93, p. 5371 CS.
Chem. Abst., vol. 74-112039D (1974).

*Primary Examiner*—Stanley J. Friedman
*Attorney, Agent, or Firm*—Merriam, Marshall & Bicknell

[57] ABSTRACT

A method for treating an inflammatory condition in a mammalian patient by administering an effective amount of a 1-aralkyl-3-amino-2-pyrazoline compound having the formula

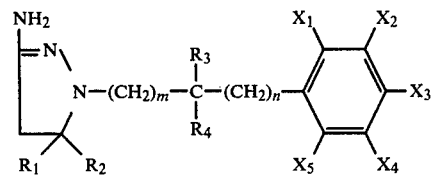

or a pharmaceutically acceptable acid addition salt thereof, wherein:

m and n are integers ranging from 0 to 6, $R_1$, $R_2$, $R_3$, $R_4$, and $R_5$, which can be the same or different, are hydrogen or lower alkyl, $X_1$, $X_2$, $X_3$, $X_4$, and $X_5$, which can be the same or different, are hydrogen, halogen, alkyl, cycloalkyl, alkoxy, alkanoyloxy, phenyl, phenoxy, benzyloxy, haloalkyl, mercaptoalkyl, amino, alkylamine, hydroxyl, nitro, and nitrile, each of $X_1$–$X_5$, when they contain carbon, having not more than 6 carbon atoms.

The compounds used in the method have unexpectedly low toxicity.

6 Claims, No Drawings

METHOD FOR TREATING INFLAMMATORY CONDITIONS

The present invention relates to a novel method for treating inflammatory conditions in a mammalian patient by administering a 1-aralkyl derivative of 3-amino-2-pyrazoline.

BACKGROUND OF THE INVENTION

As disclosed in British Pat. No. 1,324,687 and European patent application No. 22587 (published Jan. 21, 1981), certain 1-aryl derivatives of 3-amino-2-pyrazoline such as 1-phenyl-3-amino-2-pyrazoline, are known to have anti-inflammatory activity. U.S. Pat. No. 3,927,025 discloses that certain 1-aralkyl (e.g., 1-benzyl) derivatives of 3-amino-2-pyrazoline have anti-spasmodic activity in mammals.

SUMMARY OF THE INVENTION

We have found that certain 1-aralkyl derivatives of 3-amino-2-pyrazoline have anti-inflammatory activity which is equal to or greater than that of the 1-aryl derivatives heretofore known for this purpose. Surprisingly, however, the 1-aralkyl derivatives have much lower levels of toxicity, which enhances their utility for treating inflammatory conditions in mammals, including man.

According to the invention, an inflammatory condition in a mammalian patient is treated by administering to the patient an effective amount of a 1-aralkyl-3-amino-2-pyrazoline compound having the formula

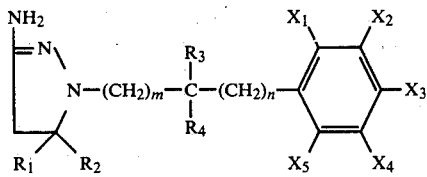

or a pharmaceutically acceptable acid addition salt thereof, wherein:

m and n are integers ranging from 0 to 6, $R_1$, $R_2$, $R_3$, $R_4$, and $R_5$, which can be the same or different, are hydrogen or lower alkyl, $X_1$, $X_2$, $X_3$, $X_4$, and $X_5$, which can be the same or different, are hydrogen, halogen, alkyl, cycloalkyl, alkoxy, alkanoyloxy, phenyl, phenoxy, benzyloxy, haloalkyl, mercaptoalkyl, amino, alkylamine, hydroxyl, nitro, and nitrile, each of $X_1$–$X_5$, when they contain carbon, having not more than 6 carbon atoms.

The anti-inflammatory activity and unexpectedly low toxicity which such compounds possess make them effective for treatment of rheumatoid arthritis and other inflammatory diseases, type III hypersensitivity diseases, and diseases in which polymorphonuclear leukocyte accumulation contributes to the pathology.

DESCRIPTION OF THE PREFERRED EMBODIMENTS

In formula I, suitable lower alkyl groups include straight or branched chain alkyl groups having 1-6 carbon atoms, such as methyl, ethyl, and isobutyl. When any of substituents $X_1$–$X_5$ contains carbon, as in alkoxy and alkylamine, the total number of carbon atoms in the substituent is not more than 6.

As used herein, the terms "alkoxy" and "alkanoyloxy" refer to the substituents

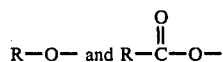

respectively, wherein R is an alkyl group.

The term "alkylamine" refers to an amino group substituted with one or two alkyl groups, as in methylamino, dimethylamino and methylethylamino. The amine group can also be substituted with an alkanoyl group, as in acetamido,

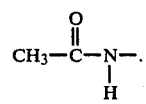

The term "cycloalkyl" as used herein refers to cyclic, saturated aliphatic radicals having 3-6 carbon atoms, as illustrated by cyclopropyl, cyclobutyl and cyclohexyl.

The term "haloalkyl" refers to an alkyl group substituted with one or more halogen atoms, such as bromomethyl, 2-dichloroethyl, and trifluoromethyl.

Preferred compounds for use in the invention are 1-benzyl-3-amino-2-pyrazoline, the 1-(p-alkylbenzyl)-3-amino-2-pyrazolines, such as 1-(3'-methylbenzyl)-3-amino-2-pyrazoline, 1-(p-phenoxybenzyl)-3-amino-2-pyrazoline, and 1-(4'-dimethylaminobenzyl)-3-amino-2-pyrazoline.

Also included within the scope of the invention are pharmaceutically acceptable acid addition salts of the compounds of formula I. Such salts can be formed with inorganic acids, such as hydrochloric acid, hydrobromic acid, sulphuric acid and nitric acid, or organic acids, such as acetic acid, lactic acid, tartaric acid, fumaric acid and maleic acid.

In general, the 1-aralkyl-3-amino-2-pyrazoline compounds used in the invention can be prepared in known fashion by the reaction of an appropriate aralkyl hydrazine with an acrylonitrile derivative in the presence of a base such as sodium hydroxide or sodium methoxide, and in a proton donating solvent, such as a lower alcohol, in accordance with the equation

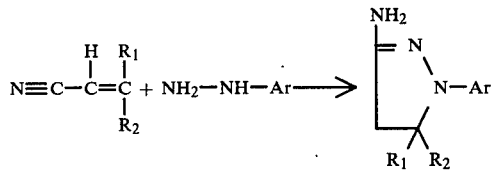

wherein Ar is

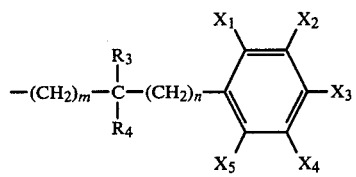

and $R_1$–$R_4$ and $X_1$–$X_4$ are as previously defined.

If the aralkyl hydrazine starting compound is reactive towards nucleophilic base, it is preferred to use a quarternary ammonium salt, such a choline, as the base and to carry out the reaction in the absence of solvent or in aprotic solvents, such as tetrahydrofuran. As an alternative procedure for use when the aralkyl hydrazine starting material is unstable, the 1-aralkyl-3-amino-2-pyrazoline compounds can be prepared by reaction of an appropriately substituted 3-amino-2-pyrazoline sulphate with the appropriate aldehyde or other carbonyl compound under reductive alkylation conditions using Adam's catalyst ($PtO_2$) in an atmosphere of hydrogen, as disclosed in British Pat. No. 1,180,876, published Feb. 11, 1970.

The compounds of the present invention have anti-inflammatory activity and an inhibitory effect on Type III hypersensitivity reactions. Accordingly, they are useful for therapy of rheumatoid arthritis, other inflammatory conditions, Type III hypersensitivity diseases, and in diseases in which polymorphonuclear luekocyte accumulation contribute to the pathology such as gouty arthritis, systemic lupus erythematosus, scleroderma, serum sickness, glomerulonephritis and hypersensitivity pneumonia. For the above-mentioned uses, the dosage administered will, of course, vary with the compound employed, the mode of administration and the severity of the condition to be treated. In general, however, satisfactory results are obtained when the compounds of formula I are administered at a dosage of about 10 to 200 mg per kg of body weight, preferably in divided doses, i.e., 3-4 times daily.

The compounds useful in the invention exhibit both oral and parenteral activity in mammalian patients, including man, and accordingly can be formulated in dosage forms for either oral or parenteral administration to such a patient. Although the active agents can be administered as pure compounds, it is advisable to combine them with a suitable pharmaceutical carrier to obtain a satisfactory size to dosage relationship.

Pharmaceutical carriers which are liquid or solid can be used. Solid carriers such as starch, sugar, talc and the like can be used to form powders. The powders can be used for direct oral administration or alternatively to make tablets or to fill gelatin capsules. Suitable lubricants like magnesium stearate, binders such as gelatin, and disintegrating agents such as sodium carbonate in combination with citric acid can be used to form tablets.

Liquid dosage forms for oral administration include emulsions, solutions, suspensions, syrups and the like, containing diluents commonly used in the art, such as water. Besides inert diluents, such preparations can also include adjuvants, such as wetting agents, emulsifying and suspending agents and sweetening, flavoring, and perfuming agents.

Preparations for parenteral administration include sterile aqueous or non-aqueous solutions. Examples of non-aqueous solvents or vehicles are propylene glycol, polyethylene glycol, vegetable oil, such as olive oil, and injectable organic esters such as ethyloleate.

The anti-inflammatory activity of the compounds used in the invention was established using the reverse passive Arthus reaction in the rat as described by G. W. Carter and R. A. Krause in Federation Proceedings, Vol. 35, page 774, 1976. Although the carrageenin rat paw edema test (Winter et al., *Proc. Soc. Exp. Biol. Med.*, 111, 554, 1962) can also be used to establish anti-inflammatory activity, the Arthus reaction, unlike carrageenin induced edema, is a well-characterized immune reaction which bears close resemblance to the pathogenesis of rheumatoid arthritis.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases, the antigen and antibody become deposited in the walls of small venules. Plasma complement is rapidly bound and activated. Within a few hours, neutrophils (PMNs) accumulate, resulting in disruption of the basement membrane of vessel walls and marked edema hemorrhage in the surrounding tissue.

Although the etiology of rheumatoid arthritis remains obscure, it is almost certain that immunological mechanisms play an important role in the pathogenesis of this disease. Therefore, inflammation induced by immunological reactions, which are believed to be important in the inflammatory processes of rheumatoid arthritis, make particularly desirable tools for the screening of potential anti-inflammatory agents. The usefulness of such a model depends on how closely it represents the underlying pathological mechanisms of rheumatoid arthritis.

Based on currently available evidence, a plausible sequence of events leading to the joint lesions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activate complement, causing the generation of a number of phlogistic and chemotactic substances. Phagocytosis of the complexes by attracted polymorphonuclear luekocytes (PMNs) leads to the release of lysosomal constituents. The enzymes released from lysosomes can erode articular cartilage and produce inflammation in the joint. The striking resemblance of these events to the Arthus phenomenon point to the utility of the orifice reaction as a screen for anti-inflammatory compounds.

The reverse passive Arthus reaction test in rats is conducted as follows. Male Sprague-Dawley rats weighing approximately 130–160 grams each are used in groups of 4. All animals are injected intravenously with 0.5 ml of 0.075% bovine serum albumin (B.S.A.) plus 0.2% Evans Blue solution. Each rat then receives an oral dose of the drug under test; one drug is administered to each group of 4 rats.

Thirty minutes after administration of the drug, each animal is injected intradermally with 0.05 ml of 1.44% anti-B.S.A. into the dorsal skin. Four hours later, the animals are sacrificed, the dorsal skin is reflexed and the lesion is excised. Two perpendicular diameters of each lesion are measured. The average diameters of the lesions from the treated groups are compared with the average diameters from a control group to determine any drug effect.

The anti-inflammatory activity of the compounds used in the invention was demonstrated by the reverse passive Arthus reaction tests in rats, as illustrated in Table 1, which also reports for comparison the activity of 1-benzyl-3-pyrazolidinone, a compound taught in the art as having anti-inflammatory activity (see East German Patent 110,868).

TABLE 1

| Compound | Dose (mg/kg of body weight) | % Inhibition Of Lesion |
| --- | --- | --- |
| 1-benzyl-3-amino-2-pyrazoline | 100 | 57 |
| 1-benzyl-3-pyrazolidinone | 100 | 28 |

Similar results can be obtained using the other active agents which come within the scope of the invention.

The anti-inflammatory activity of the compounds useful in the invention was also demonstrated (Table 2) by using a modification of the carrageenin pleurisy assay described by Vinegar et al. (*Proc. Soc. Exp. Biol. Med.*, 143: 711, 1973). Also tested for comparison was phenylbutazone, a compound known to have anti-inflammatory activity.

TABLE 2

| Compound | Dose (mg/kg) | % Inhibition Volume Exudate | Cells |
| --- | --- | --- | --- |
| 1-benzyl-3-amino-2-pyrazoline | 120 | 76 | 55 |
| phenylbutazone | 100 | 59 | 13 |

In contrast to 1-aryl derivatives of 3-amino-2-pyrazoline, which also may have anti-inflammatory activity, the 1-alkaryl compounds of the invention are significantly less toxic at equivalent dosage levels. The lesser toxicity of the 1-alkaryl derivatives is illustrated by the data of Table 3, which gives the fatality ratio in rats when the compounds were administered in the indicated dosages. As shown, the 1-aralkyl compound (b) of the invention was markedly less toxic than a typical 1-aryl compound (a) of the prior art.

TABLE 3

| Compound | Dose (mg/kg) | Fatality Ratio |
| --- | --- | --- |
| (a) 1-(m-trifluoromethylphenyl)-3-amino-2-pyrazoline | 285 | 8/10 |
| (b) 1-benzyl-3-amino-2-pyrazoline | 512 | 0/10 |

The preparation of representative compounds useful in the invention is illustrated by the following examples.

EXAMPLE 1

1-benzyl-3-amino-2-pyrazoline hydrochloride

To a solution of sodium ethoxide, prepared by dissolving sodium (2.5 g) in ethanol (600 ml), were added benzylhydrazine (50 g) and acrylonitrile (23.9 g) under nitrogen. The solution was refluxed overnight. The solvent was removed under vacuum and the residue was treated with water and extracted with methylene chloride. The extracts were dried over magnesium sulphate and concentrated to one-third of the original volume. A solution of ethereal hydrochloric acid (250 ml) was added. The precipitate was isolated by decantation and crystallized from ethanol to give 1-benzyl-3-amino-2-pyrazoline hydrochloride, m.p. 232°–234° C.

The free base, if desired, can be recovered from the acid addition salt in conventional fashion, e.g., by dissolving the salt in water, neutralizing the acid with a suitable base, such as NaOH, extracting the pyrazoline base with a suitable organic solvent, such as methylene chloride, and evaporating the solution to dryness.

EXAMPLE 2

Using the procedure of Example 1, the substituted benzylhydrazines set out below were reacted with acrylonitrile to produce the indicated products:

| Benzylhydrazines | Products |
| --- | --- |
| 2-methoxybenzyl hydrazine | 1-(2'-methoxybenzyl)-3-amino-2-pyrazoline hydrochloride, m.p. 222–225° |
| 2-acetoxybenzylhydrazine | 1-(2'-acetoxybenzyl)-3-amino-2-pyrazoline hydrochloride |
| 3-methylbenzylhydrazine | 1-(3'-methylbenzyl)-3-amino-pyrazoline hydrochloride, m.p. 184–188° |
| 3-phenoxybenzylhydrazine | 1-(3'-phenoxybenzyl)-3-amino-2-pyrazoline hydrochloride, m.p. 196–199° |
| 3-cyanobenzylhydrazine | 1-(3'-cyanobenzyl)-3-amino-2-pyrazoline hydrochloride |
| 3-trifluoromethylbenzyl hydrazine | 1-(3'-trifluoromethylbenzyl)-3-amino-2-pyrazoline hydrochloride, m.p. 188° |
| 2-bromobenzylhydrazine | 1-(2'-bromobenzyl)-3-amino-2-pyrazoline hydrochloride, m.p. 239–241° |
| 2-fluorobenzylhydrazine | 1-(2'-fluorobenzyl)-3-amino-2-pyrazoline hydrochloride, m.p. 198.5° |
| 2-chlorobenzylhydrazine | 1-(3'-chlorobenzyl)-3-amino-2-pyrazoline hydrochloride, m.p. 178–180° |
| 3-t-butylbenzylhydrazine | 1-(3'-t-butylbenzyl)-3-amino-2-pyrazoline hydrochloride |
| 3-phenylbenzylhydrazine | 1-(3'-phenylbenzyl)-3-amino-2-pyrazoline hydrochloride |
| 4-methylbenzylhydrazine | 1-(4'-methylbenzyl)-3-amino-2-pyrazoline hydrochloride, m.p. 231–232° |
| 2-chlorobenzylhydrazine | 1-(2'-chlorobenzyl)-3-amino-2-pyrazoline hydrochloride, m.p. 223–225° |
| 3-fluorobenzylhydrazine | 1-(3'-fluorobenzyl)-3-amino-2-pyrazoline hydrochloride, m.p. 191–192° |

EXAMPLE 3

1-(3'-hydroxybenzyl)-3-amino-2-pyrazoline hydrochloride

Adam's platinum (0.2 g) was added to a mixture of 3-amino-2-pyrazoline sulphate (14.7 g) and 3-hydroxybenzaldehyde (10.58 g) in water (50 ml) and methanol (150 ml). The mixture was shaken in an atmosphere of hydrogen at a temperature of 25°–35° C. Under atmospheric pressure, one mole of hydrogen per mole of 3-amino-2-pyrazoline sulphate was taken up in 4–6 hours. The catalyst was removed by filtration and the solvent was removed under vacuum. The residue was taken up in methanol and sodium hydroxide (6.4 g) was added. The precipitate was separated by filtration. The filtrate was concentrated under vacuum and the residue was treated with ethereal hydrochloric acid-ethanol to give 1-(3'-hydroxybenzyl)-3-amino-2-pyrazoline hydrochloride.

EXAMPLE 4

Using the procedure of Example 3, the following aldehyde derivatives were allowed to react with 3-amino-2-pyrazoline sulfate to produce the indicated products.

| Aldehydes | Products |
|---|---|
| α-phenylpropion aldehyde | 1-(β-methylphenethyl)-3-amino-2-pyrazoline hydrochloride |
| 4-carbomethoxybenzaldehyde | 1-(4-carbomethoxybenzyl)-3-amino-2-pyrazoline hydrochloride |
| 3-methoxybenzaldehyde | 1-(3-methoxybenzyl)-3-amino-2-pyrazoline hydrochloride, m.p. 191–192° |
| phenylacetaldehyde | 1-phenethyl-3-amino-2-pyrazoline hydrochloride, m.p. 113–114° |
| 4-dimethylaminobenzaldehyde | 1-(4'-dimethylaminobenzyl)-3-amino-2-pyrazoline hydrochloride |
| 4-acetamidobenzaldehyde | 1-(4'-acetamidobenzyl)-3-amino-2-pyrazoline hydrochloride |
| 3,5-di-t-butyl-4-hydroxybenzaldehyde | 1-(3',5'-di-t-butyl-4'-hydroxybenzyl)-3-amino-2-pyrazoline hydrochloride |
| 3,4-dimethoxybenzaldehyde | 1-(3',4'-dimethoxybenzyl)-3-amino-2-pyrazoline hydrochloride |
| 3-methoxy-4-phenoxybenzaldehyde | 1-(3'-methoxy-4'-phenoxybenzyl)-3-amino-2-pyrazoline hydrochloride |
| 2,5-dimethylbenzaldehyde | 1-(2',5'-dimethylbenzyl)-3-amino-2-pyrazoline hydrochloride m.p. 158–9° |
| 3-fluoro-4-methoxybenzaldehyde | 1-(3'-fluoro-4'-methoxybenzyl)-3-amino-2-pyrazoline hydrochloride |
| 3-cyclohexylbenzaldehyde | 1-(3'-cyclohexylbenzyl)-3-amino-2-pyrazoline hydrochloride |
| phenylacetone | 1-(α-methylphenethyl)-3-amino-2-pyrazoline hydrochloride |

EXAMPLE 5

(3'-methoxybenzyl)-3-amino-2-pyrazoline hydrochloride

A mixture of 3-methoxybenzylhydrazine (15.2 g), acrylonitrile (10.6 g) and 20 drops of 50% methanolic solution of choline base was heated at 110° in an oil bath for 1 hour. A 25% hydrochloric acid solution (35 ml) was added and the mixture was refluxed for an additional hour. After cooling, the mixture was basified with sodium hydroxide pellets. The precipitate was isolated, washed with water and dried. A solution of the dried product in ethanol was treated with ethereal hydrochloric acid to give 1-(3'-methoxybenzyl)-3-amino-2-pyrazoline hydrochloride.

EXAMPLE 6

Using the procedure of Example 5, the following benzylhydrazine derivatives were reacted with acrylonitrile to produce the indicated products:

| Benzylhydrazines | Products |
|---|---|
| 3-nitrobenzylhydrazine | 1-(3'-nitrobenzyl)-3-amino-2-pyrazoline hydrochloride |
| 3-fluorobenzylhydrazine | 1-(3'-fluorobenzyl)-3-amino-2-pyrazoline hydrochloride |
| 4-phenylbenzylhydrazine | 1-(4'-phenylbenzyl)-3-amino-2-pyrazoline |
| 4-phenoxybenzylhydrazine | 1-(4'-phenoxybenzyl)-3-amino-2-pyrazoline hydrochloride, m.p. 216–218° |
| 4-methoxybenzylhydrazine | 1-(4'-methoxybenzyl)-3-amino-2-pyrazoline hydrochloride, m.p. 195–196° |
| 3-bromobenzylhydrazine | 1-(3'-bromobenzyl)-3-amino-2-pyrazoline hydrochloride, m.p. 176–180° |
| 3-benzyloxybenzylhydrazine | 1-(3'-benzyloxybenzyl)-3-amino-2-pyrazoline hydrochloride, m.p. 173–176° |

EXAMPLE 7

1-(α-methylbenzyl)-3-amino-2-pyrazoline hydrochloride

A. d,l-α-methylbenzylhydrazine

To a solution of α-methylbenzylamine (12.1 g) in concentrated hydrochloric acid (90 ml) and water (90 ml) cooled to 0° C. was added a solution of sodium nitrite (6.9 g) in water (90 ml). The mixture was stirred for an additional 5 minutes after the completion of the addition and then was added to a solution of stannous chloride (47.5 g) in concentrated hydrochloric acid (50 ml) cooled to 0° C. The precipitate was isolated by filtration and added to water. The aqueous solution was basified with sodium hydroxide pellets to pH 9 and extracted with methylene chloride. The organic extracts were dried over sodium sulphate and concentrated under vacuum to give d,l-α-methylbenzylhydrazine, b.p. 76°/1 mm Hg.

B. 1-(α-methylbenzyl)-3-amino-2-pyrazoline hydrochloride

To a solution of sodium ethoxide prepared by dissolving sodium (0.128 g) in ethanol (800 ml) was added d,l-α-methylbenzylhydrazine (8 g) and acrylonitrile (2.96 g). The solution was refluxed under nitrogen for 12 hours, then cooled and ethanolic hydrochloric acid (10 ml) was added. The precipitate was filtered. The filtrate was concentrated and the residue was triturated with ether to give a solid which on crystallization from ethanol gave d,l-1-(α-methylbenzyl)-3-amino-2-pyrazoline hydrochloride, m.p. 223°–225° C.

EXAMPLE 8

Using the procedure of Example 7, the following amines were used to prepare the corresponding hydrazines which on reaction with acrylonitrile gave the indicated products:

| Amines | Products |
|---|---|
| d-α-methylbenzylamine | d-1-(α-methylbenzyl)-3-amino-2-pyrazoline hydrochloride |
| l-α-methylbenzylamine | l-1-(α-methylbenzyl)-3-amino-2-pyrazoline hydrochloride |
| 3-phenylpropylamine | 1-(γ-phenylpropyl)-3-amino-2-pyrazoline hydrochloride, m.p. 164–165° |
| 4-phenylbutylamine | 1-(δ-phenylbutyl)-3-amino-2-pyrazoline hydrochloride, m.p. 160–161° |

EXAMPLE 9

Using the procedure of Example 1, the following acrylonitrile derivatives were reacted with benzylhydrazine to yield the indicated products:

| Nitriles | Products |
|---|---|
| β-methylacrylonitrile | 1-benzyl-5-methyl-3-amino-2-pyrazoline, m.p. 152–153° |
| β-dimethylacrylonitrile | 1-benzyl-5-dimethyl-3-amino- |

| Nitriles | Products |
|---|---|
| | 2-pyrazoline hydrochloride |

The foregoing detailed description has been given for clearness of understanding only, and no unnecessary limitations should be understood therefrom as modifications will be obvious to those skilled in the art.

What is claimed:

1. A method for treating an inflammatory condition in a mammalian patient which comprises administering to a patient requiring such treatment an effective amount of a compound having the formula

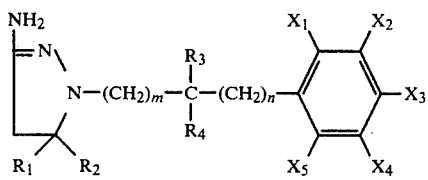

or a pharmaceutically acceptable acid addition salt thereof, wherein:

m and n are integers ranging from 0 to 6, $R_1$, $R_2$, $R_3$, $R_4$ and $R_5$, which can be the same or different, are hydrogen or lower alkyl, $X_1$, $X_2$, $X_3$, $X_4$ and $X_5$, which can be the same or different, are hydrogen, halogen, alkyl, cycloalkyl, alkoxy, alkanoyloxy, haloalkyl, phenyl, phenoxy, benzoyloxy, mercaptoalkyl, amino, alkylamine, hydroxyl, nitro, and nitrile, each of $X_1$–$X_5$, when they contain carbon, having not more than 6 carbon atoms.

2. The method of claim 1 wherein said compound is selected from 1-benzyl-3-amino-2-pyrazoline
1-(2'-methoxybenzyl)-3-amino-2-pyrazoline
1-(2'-acetoxybenzyl)-3-amino-2-pyrazoline
1-(3'-methylbenzyl)-3-amino-2-pyrazoline
1-(3'-phenoxybenzyl)-3-amino-2-pyrazoline
1-(3'-cyanobenzyl)-3-amino-2-pyrazoline
1-(3'-trifluoromethylbenzyl)-3-amino-2-pyrazoline
1-(2'-bromobenzyl)-3-amino-2-pyrazoline
1-(2'-fluorobenzyl)-3-amino-2-pyrazoline
1-(3'-chlorobenzyl)-3-amino-2-pyrazoline
1-(3'-t-butylbenzyl)-3-amino-2-pyrazoline
1-(3'-phenylbenzyl)-3-amino-2-pyrazoline
1-(3'-hydroxybenzyl)-3-amino-2-pyrazoline
1-(β-methylphenethyl)-3-amino-2-pyrazoline
1-(4-carbomethoxybenzyl)-3-amino-2-pyrazoline
1-phenethyl-3-amino-2-pyrazoline
1-(4'-dimethylaminobenzyl)-3-amino-2-pyrazoline
1-(4'-acetamidobenzyl)-3-amino-2-pyrazoline
1-(3',5'-di-t-butyl-4'-hydroxybenzyl)-3-amino-2-pyrazoline
1-(3',4'-dimethoxybenzyl)-3-amino-2-pyrazoline
1-(3'-methoxy-4'-phenoxybenzyl)-3-amino-2-pyrazoline
1-(2',4'-dimethylbenzyl)-3-amino-2-pyrazoline
1-(3'-fluoro-4'-methoxybenzyl)-3-amino-2-pyrazoline
1-(3'-cyclohexylbenzyl)-3-amino-2-pyrazoline
1-(α-methylphenethyl)-3-amino-2-pyrazoline
1-(3'-methoxybenzyl)-3-amino-2-pyrazoline
1-(3'-nitrobenzyl)-3-amino-2-pyrazoline
1-(3'-fluorobenzyl)-3-amino-2-pyrazoline
1-(4'-phenylbenzyl)-3-amino-2-pyrazoline
1-(4'-phenoxybenzyl)-3-amino-2-pyrazoline
d,l-1-(α-methylbenzyl)-3-amino-2-pyrazoline
d-1-(α-methylbenzyl)-3-amino-2-pyrazoline
l-1-(α-methylbenzyl)-3-amino-2-pyrazoline
1-(γ-phenylpropyl)-3-amino-2-pyrazoline
1-(γ-phenylbutyl)-3-amino-2-pyrazoline
1-benzyl-5-methyl-3-amino-2-pyrazoline
1-benzyl-5-dimethyl-3-amino-2-pyrazoline and pharmaceutically acceptable acid addition salts thereof.

3. The method of claim 1 wherein m and n are both zero, $R_1$, $R_2$, $R_3$ and $R_4$ are hydrogen, and $X_3$ is lower alkyl.

4. The method of claim 1 wherein said compound is 1-benzyl-3-amino-2-pyrazoline or a pharmaceutically acceptable acid addition salt thereof.

5. The method of claim 1 wherein said compound is 1-(4'-dimethylaminobenzyl)-3-amino-2-pyrazoline or a pharmaceutically acceptable acid addition salt thereof.

6. The method of claim 1 wherein said compound is 1-(p-phenoxybenzyl)-3-amino-2-pyrazoline or a pharmaceutically acceptable acid addition salt thereof.

* * * * *